US006814998B1

(12) United States Patent
Ozawa et al.

(10) Patent No.: US 6,814,998 B1
(45) Date of Patent: Nov. 9, 2004

(54) SOYBEAN EMBRYO FAT/OIL AND PROCESS FOR PRODUCING SOYBEAN MATERIAL WITH HIGH EMBRYO CONCENTRATION

(75) Inventors: Yoichi Ozawa, Kawasaki (JP); Akihiro Nakatani, Yokohama (JP); Hitoshi Sato, Kawasaki (JP); Osamu Mori, Kawasaki (JP); Yukio Akiyama, Tokyo (JP); Yasushi Morinaga, Kawasaki (JP); Yuji Nakata, Yokohama (JP)

(73) Assignee: Ajinomoto Co., Inc., Tokyo (JP)

( * ) Notice: Subject to any disclaimer, the term of this patent is extended or adjusted under 35 U.S.C. 154(b) by 148 days.

(21) Appl. No.: 09/868,643

(22) PCT Filed: Jul. 5, 2000

(86) PCT No.: PCT/JP00/04453

§ 371 (c)(1),
(2), (4) Date: Oct. 5, 2001

(87) PCT Pub. No.: WO01/32032

PCT Pub. Date: May 10, 2001

(30) Foreign Application Priority Data

Oct. 28, 1999 (JP) ............................................ 11-306248
Apr. 28, 2000 (JP) ....................................... 2000-128722

(51) Int. Cl.$^7$ ............................................... A23D 9/00
(52) U.S. Cl. ........................... 426/601; 426/417; 554/8; 554/9
(58) Field of Search ................................ 426/601, 634, 426/417; 554/8, 9

(56) References Cited

U.S. PATENT DOCUMENTS

| | | | |
|---|---|---|---|
| 3,993,756 A | | 11/1976 | Kaneda et al. |
| 4,495,207 A | * | 1/1985 | Christianson et al. ....... 426/312 |
| 4,556,573 A | * | 12/1985 | Bartesch et al. ............ 426/467 |
| 5,795,969 A | * | 8/1998 | Fehr et al. ...................... 554/9 |
| 5,952,230 A | | 9/1999 | Kim et al. |
| 6,326,035 B1 | | 12/2001 | Nakatani et al. |

FOREIGN PATENT DOCUMENTS

| | | | |
|---|---|---|---|
| JP | 53-115836 | | 10/1978 |
| JP | 59-82063 | | 5/1984 |
| JP | 59-147647 | | 8/1984 |
| JP | 60-78542 | | 5/1985 |
| JP | 60-126078 | * | 7/1985 |
| JP | 62-100256 | * | 5/1987 |
| JP | 09-182562 | | 7/1997 |
| JP | 11-196803 | * | 11/1999 |

OTHER PUBLICATIONS

Kajimoto, 1984. J Jpn Oil Chem Soc. 33(8)518. translation.*
Tokue, C. 1987. J. Japanese Society of Nutrition and Food Science 40(4)313.*
Smith, Allan, 1972. Soybeans: Chemistry and Technology vol. 1. The AVI Publishing Company, Inc, Westport CT. p. 315.*
G. Kajimoto, et al., J. Jpn. Oil. Chem. Soc., vol. 33, No. 8, pp. 518–822, XP–001145941, "Sterol Compositions in Lipids of Cotyledon, Embryo and Seed Coat from Soybean, Cotton and Sunflower Seed", 1984.
E. Fedeli, et al., A Rivista Italiana Delle Sostanze Grasse, vol. 43, No. 11, pp. 509–511, "I Componenti Minori Dell'Insaponificabile Delle Differenti Parti Anatomiche del Seme di Soja", Nov. 1966 (with English Abstract and summarized English translation).
C. Tokue, et al., J. Jpn. Soc. Nutr. Food Sci., vol. 40, No. 4, pp. 313–319, "Properties Peculiar to Lipids in Soybeans of Beeson Species", 1987 (with English Abstract and English concise explanation).
G. Kajimoto, et al., J. Jap. Soc. Nutr. Food Sci., vol. 35, No. 5, pp. 345–350, "Changes in the Contents and Compositions of Lipids, Fatty Acids, Tocopherols and Sterols in Soybean Seed During Maturation", 1982 (with English Abstract and concise explanation).
U.S. patent application Ser. No. 09/807,997, filed Aug. 8, 2001, pending.
U.S. patent application Ser. No. 09/968,979, filed Oct. 3, 2001, pending.
U.S. patent application Ser. No. 09/868,643, filed Oct. 5, 2001, pending.

* cited by examiner

Primary Examiner—Carolyn Paden
(74) Attorney, Agent, or Firm—Oblon, Spivak, McClelland, Maier & Neustadt, P.C.

(57) ABSTRACT

The purpose of the present invention is to extract oil from the soybean material containing soybean germ as a main component, and to utilize it.

The present invention relates to a method for producing a soybean material, comprising crudely crushing selected soybeans into a size of less than ½, and separating and concentrating a soybean germ fraction by means of sieving, sorting with air, separation based on the grain shape and the like, to the soybean germ fraction produced by said method, to oil prepared form the soybean material containing soybean germ as a main component, to oil containing 0.8% by weight or more of sterols' content, and to foods containing said oil.

21 Claims, 5 Drawing Sheets

Chromatogram

Fig.1

Chromatogram

SOYBEAN EMBRYO FAT/OIL AND PROCESS FOR PRODUCING SOYBEAN MATERIAL WITH HIGH EMBRYO CONCENTRATION

TECHNICAL FIELD

The present invention relates to a method for producing germ-enriched soybean material, comprising separating and concentrating a germ fraction (although the "germ" should be academically called a "hypocotyle", the term "germ" is used in the present specification in the same meaning as the hypocotyle), to oil prepared from germ-enriched soybean material, to soybean oil containing 0.8% by weight or more of sterol, to a cholesterol-lowering agent comprising said oil as an effective component, and to a food containing said oil.

BACKGROUND ART

Like the other oil seeds, soybean consists of the parts of a cotyledon (ca.90%), a germ (ca.2%) and a hull (ca.8%). The soybean is used as material for soybean oil, after its hull is removed but the cotyledon and the germ that are rich in oil are not separated with each other.

When the oil is produced from the soybean, foreign substances such as stem, sheath and other seeds are first removed from a starting soybean material in a selection step for improving quality of a final oil product and defatted cake. Then, the material is provided with elasticity by being subjected to, for example, a heating treatment, crushed by means of a crushing roller or rubber roller and separated into the hull, cotyledon and germ parts. The hull, which contains components such as a pigment that will adversely affect the quality of oil, is removed by means of a vibrating sieve or a sorting apparatus with air. The cotyledon and germ are flaked altogether to destruct their structures and to ease extraction of oil, followed by the extraction with n-hexane to give a crude oil, which is finally purified to yield the soybean oil.

Japanese Patent Laid-Open Application Sho.59 (1984)-82063 and Japanese Patent Laid-Open Application Hei.11 (1999)-196803 disclose a method for obtaining the germ part from half-cut soybeans by means of a sieve or sorting with air. In the method the germ part may be separated at a high concentration without suffering any damage. However, it is impossible to treat a large amount of the half-cut soybeans in just one crushing step. Further, a collecting rate of the germ attached to the hull is very low, increasing a load of a flaking machine. For these reasons, it is difficult to extract oil from the germ-enriched part obtained from the half-cut soybeans in view of processing capacity and performance management.

Japanese Patent Publication Sho.56 (1981)-39176 discloses a method for the concentration of soybean germ by sorting crudely crushed soybeans with air and separating a fraction of 14-60 mesh by means of a sieve. However, since the method will seriously hurt the germ part, the crudely crushed soybeans have to be immediately subjected to the next step. And, the size of the separated soybean fraction is so fine that an amount of the extracted oil will be small, increasing a load in a step for removing a solvent from meal.

Japanese Patent Laid-Open Application Sho.62(1987)-100256 discloses a method comprising treating crudely crushed soybeans at a high temperature and a high pressure for a certain period of time, releasing them under a low pressure to expand only the germ part, followed by separation of the germ and cotyledon by making use of the difference in their specific gravity. However, it is very dangerous to perform this method at the high temperature and high pressure, and nutritious elements in the germ will very likely be destroyed under these conditions. Further, it will disadvantageously take a heavy load to purify the oil that has been extracted from a burned cotyledon part into odorless and tasteless soybean salad oil.

Soybean is food stuff that is very nutritious, and has been widely used as materials for various kinds of foods.

Up to now, a composition of phytosterols in the oil extracted from each part of the cotyledon, germ and hull, respectively, has been analyzed and reported (Kajimoto, G., et al., J. Jpn Oil Chem. Soc., 33 (8) 518 (1984)). But, Kajimoto, et al. did not disclose a total amount of sterol contained in said oil extracted from each part of soybean. Further, it did not disclose any cholesterol lowing effects of the oil extracted from soybean, either.

On the other hand, it is already known that oil that is supplemented with sterol (soybean sterol) that is obtained from deodorized distillate produced as a by-product during the production of soybean "tempura oil" (Japanese deep frying oil) may lower the cholesterol level in a body (Shibuya, et al., Journal of Kagawa Nutrition university 14, 173 (1983)).

The purposes of the present invention is therefore to improve a processing capacity in a crushing step, to reduce loss of the germ due to its attachment to the soybean (hull), to reduce an amount of the load in a flaking step and solvent-removing step, and to lower an amount of remaining oil in an extraction step when a soybean germ fraction is obtained from the soybean material. As a result, both the oil extracted from the germ and that from the cotyledon may be obtained without any loss, which may be then purified into soybean oil with a good taste.

Another purpose of the present invention is to provide oil that is prepared from the above fraction containing the soybean germ at a high concentration as a soybean material.

The present inventors have evaluated the above oil in an animal test with respect to its cholesterol lowering effects in a body, and found unexpectedly that it shows the cholesterol lowering effect in the body at a smaller amount of sterol contained therein than that described in the prior documents. Another purpose of the present invention is therefore to provide an agent containing said oil as an effective component for lowering cholesterol in the body of animals.

DISCLOSURE OF THE INVENTION

The present invention relates to a method for producing a soybean material, comprising crudely crushing a starting soybean material or its selected seeds from which foreign substances have been removed, into a size of less than ½, preferably ⅟₁₆ or more and less than ½, more preferably ⅛ or more and less than ¼ of the original one, and separating and concentrating a soybean germ fraction.

In the above production method, the separation and concentration of the soybean germ fraction may be done after crudely crushing and flaking.

The present invention is further related to oil or soybean oil prepared from a soybean material containing 15~80% by weight, preferably 30~80% by weight, more preferably 40~80% by weight of the germ content.

The present inventors have found that said soybean oil according to the present invention originally contains 0.8% by weight or more, preferably 1.2% by weight or more, more preferably 2.5% by weight or more of a total sterol content without any addition of the sterol during its production steps.

Considering that the sterol content of a usual soybean tempura oil is about 0.4% by weight, the content of sterols in the soybean oil according to the present invention is two—six times as much as that in the usual soybean tempura oil.

Accordingly, the present invention relates to a soybean oil containing 0.8% by weight or more, preferably 1.2% by weight or more, more preferably 2.5% by weight or more of a total sterol content.

The term "total sterol" in the present specification means eight kinds of sterols in total, that is, β-Sitosterol, Campesterol, Stigmasterol, Δ7-Stigmastenol, Brassicasterol, Δ7-Avenasterol, Citrostadienol and Cholesterol.

The soybean oil according to the present invention may contain any amount of other sterols than the above eight ones, and their reduced substances and their esters.

The soybean oil of the present invention is characterized by containing tocopherol in an amount of 100 mg or more, preferably 130–300 mg per 100 g of the soybean oil.

On the other hand, the usual soybean tempura oil contains about 80–170 mg of tocopherols per 100 g of the oil.

The present invention further relates to an agent for lowering cholesterol in the body, especially in serum and liver, which comprises as an effective component the oil prepared from the soybean material containing 15% by weight or more of the germ content.

The present invention still further relates to various kinds of foods such as a nutritional supplemented food, a nutritional fortified food, and foods for specified health use, which contain the oil prepared from the soybean material containing 15% by weight or more of the germ content.

BEST MODE FOR CARRYING OUT THE INVENTION

The soybean material containing 15–80% by weight of the germ content, which is to be used as a material for the preparation of soybean oil according to the present invention, is produced as follows.

First, the starting soybean material (whole soybean) may be optionally selected by removing foreign substances (contaminants) such as stem, sheath, weeds, sands, metal particles and small stones.

Next, the thus selected starting soybean material (the selected seeds) is heated, dried, peeled or crudely crushed by means of any known apparatus making use of friction, impact stress, shearing stress and the like.

The starting soybean material is crudely crushed into the size of less than ½, preferably ¹⁄₁₆ or more and less than ½, more preferably ⅛ or more and less than ¼ of the original one, and separating and concentrating the soybean germ fraction. The starting soybean material is crudely crushed into the size of less than ½ in order to, for example, improve the processing capacity in a crushing step, to reduce the loss of the germ due to its attachment to the soybean hull, and to reduce the amount of the load in the flaking step. The size of "less than ½" means that half-cut soybeans (½ size of the original soybean) are substantially excluded from the crudely crushed soybeans.

The advantages effected by the crude crushing of the starting soybean material into a size of less than ½, preferably ¹⁄₁₆ or more and less than ½, more preferably ⅛ or more and less than ¼ of the original one are summarized in Table 1 below. In Table 1, "◎", "○", "Δ", and "X" mean "more preferable", "preferable", "usual", and "bad", respectively.

TABLE 1

|  | ½ or more | less than ½ and ¼ or more | less than ¼ and ⅛ or more | less than ⅛ and ¹⁄₁₆ or more | Less than ¹⁄₁₆ |
|---|---|---|---|---|---|
| Purity of germ | ◎ | ○ | ○ | ○ | Δ |
| Damage of germ | ◎ | ○ | ○ | ○ | Δ |
| Processing capacity in a crushing step | Δ | ○ | ◎ | ○ | Δ |
| Attachment of germ to soybean hull | x | ○ | ◎ | ○ | Δ |
| Workload in a flaking step | x | ○ | ◎ | ○ | Δ |
| Extraction efficiency | ○ | ◎ | ◎ | ○ | x |

The heating and drying of the starting soybean material is usually carried out for 4–8 hours at 40–80° C.

The crudely crushed soybean is then subjected to at least one step with a separating apparatus such as the sieve and the sorting apparatus with air by making use of difference in the specific gravity, grain size and grain shape in order to remove the hull and cotyledon and to separate and concentrate the soybean germ fraction containing a certain amount of the germ. As a result, the soybean material according to the present invention is produced. In this case, the hull and germ may be further separated with each other by slightly destroying the hull having the germ attached thereto, removing the hull with the above separating apparatus, followed by separating and concentrating the soybean germ fraction containing a large amount of the germ.

When the separating apparatus based on the difference in grain size is used, the soybean germ fraction containing the large amount of the germ may be separated and concentrated by collecting fractions of 7 mesh (2.80 mm) or less, and further collecting fractions of 10–14 mesh (1.70 mm–1.18 mm) with the sieve. The size of the mesh in the sieve for fractions to be collected depends on a degree of the crude crushing, and 14–16 mesh may be used for the same purpose.

The thus produced soybean germ fraction containing the germ as a main component contains at least 15% by weight of the germ, and may be used as the soybean material for the preparation of the soybean oil according to the present invention. The above soybean germ fraction may also contain other components consisting mainly of cotyledon and hull at various constituting ratios depending on the separating and concentrating conditions, which are also used as material for the soybean oil.

The soybean material according to the present invention may

The soybean material according to the present invention may further comprise, in addition to the material derived from soybean, other germ materials derived from, for example, corn, wheat, rice, And rapeseed at an appropriate ratio for extraction of the oil according to the present invention.

The soybean material thus produced is then heated for several seconds—about 60 minutes, for example, at 40~100° C., flaked, and contacted with an organic solvent such as n-hexane to extract an oil component or a crude oil. Alternatively, the flake may be subjected to heating and puffing by means of an expander, followed by the extraction with the organic solvent or carbonated liquid to give the crude oil.

Purified oil may be prepared by degumming, alkali refining, bleaching and deodorizing of the crude oil in a conventional manner known to those skilled in the art.

The agent or composition according to the present invention has an activity for lowering the level of cholesterol in the body, especially in serum and liver. The present agent may comprise various kinds of pharmaceutically acceptable auxiliaries and additives, which are known to those skilled in the art, in addition to the oil according to, the present invention as an effective component. The auxiliaries and additives may be in the form of solid, liquid or gel depending on their kinds.

A dose of the cholesterol-lowering agent according to the present invention depends on the level of cholesterol in the body, age, sex, physical conditions of a subject, 3–30 g in terms of the soybean oil per one day for an adult being appropriate. An administration route may be optionally selected such as orally, etc.

Especially, the cholesterol-lowering agent has an activity for significantly lowering the level of cholesterol in the serum.

The various kinds of foods according to the present invention such as usual foods, the nutritional supplemented food, the nutritional fortified food, and the foods for specified health use may comprise any known components that are acceptable in view of food hygiene, such as food additives, foodstuffs and the like.

The foods of the present invention may take various kinds of shapes or forms depending on the kinds of their components, such as mayonnaise, margarine, spread, dressing, oil for frying, bread, hamburger, solid like confectionaries, liquid, emulsion, and gel. The content of the oil according to the present invention in the foods may be optionally determined by their manufacturers, depending on the kinds of the foods.

Furthermore, the soybean oil according to the present invention may be combined for use with various kinds of germ oils such as corn germ oil, wheat germ oil, rice germ oil, and rapeseed germ oil; and usual soybean oil, rapeseed oil and sesame oil.

The present invention will be further described by referring to the following examples, which shall not be construed to limit the scope of the present invention at all.

Oil components of the examples were analyzed with by Standard Methods for the Analysis of Fats, Oils and Related Materials: Japan Oil Chemists' Society (1996). The analysis of some of the tocopherol components marked with "*" and sterols was carried out by Japan Food Analysis Center, while the rest of the tests was made by the present inventors themselves. The term "%" in the examples means "% by weight."

EXAMPLE 1

Three kinds of the soybean oils according to the present invention were prepared by using the soybean materials having different contents of the soybean germ, and they were studied with respect to their cholesterol-lowering effects in an animal test. The soybean tempera oil and cotyledon oil were used in the same test as comparison.

(Production of Material)

Selected whole soybeans were heated for 30~60 min at 80° C., and crudely crushed by being put through a rubber roller while their hulls were peeled away simultaneously due to shearing stress applied to them. After a fraction containing the germ and hull as main components was separated and collected by sorting with air, a hull part was removed by sorting with air and a germ part was concentrated. A part of the thus obtained soybean material was taken as a sample. The sample was separated into parts such as germ, and the contents of germ, cotyledon and the other parts such as hull were determined to be about 70% by weight, about 25% by weight and about 5% by weight, respectively.

Alternatively, the selected whole soybeans were heated for 30~60 min at 80~100° C., crudely crushed into a size of less than ½ of the original one to give a mixture of hull, germ and cotyledon. The hull part was then removed form the mixture by means of sorting with air, and fractions of more than 7 mesh were removed by means of a sieve so as to collect fractions of 7 mesh or less (Yield: 21.5%).

Then, the fractions of 10–14 mesh were obtained by means of a vibrating sieve or vibrating sifter, and the co-existing hull was removed by the sorting with air to give a germ fraction that corresponds to 30.4% of the fractions of 7 mesh or less. A part of the thus obtained soybean material was taken as a sample. The sample was separated into parts such as germ, and the and about 5% by weight, respectively. The cotyledon part that had been obtained separately was added to the above soybean material containing about 40% by weight of the germ content to give a soybean material containing about 20% by weight of the germ content.

(Preparation of Oils)

The above soybean materials having various germ concentrations were heated at 60° C. and pressed into flakes with 0.2~0.3 mm in thickness by means of a flaking-roller. The flakes were treated with n-hexane for one hour at 50° C. to give an oil component. The resulting cake was also treated in the same way to give an oil component. These two oil components were then combined to give micelle. The resulting micelle was concentrated at 50° C. and 100~150 mmHg, further concentrated for 1~2 hours at 60–80° C. under a reduced pressure with an aspirator, and finally heated at 60–70° C. under a reduce pressure with a vacuum pump to reversibly remove remaining n-hexane and give a crude oil.

The crude oil prepared from the soybean material containing 40% by weight of the germ content was mixed with phosphoric acid (0.1%), stirred for 15 min at 70° C., mixed with distilled water, stirred for 30 min at 70° C. and centrifuged to remove a gummy component. The resulting oil was then mixed with phosphoric acid (0.1%), stirred for 15 min at 75° C., mixed with NaOH solution (normal amount) at 26° C., stirred for 20 min at 70° C. and centrifuged. The resulting supernatant was mixed with distilled water (5% of the total), washed for one min at 80° C. and centrifuged. The resulting supernatant was mixed with activated earth (2%), stirred for 30 min at 80° C. under a reduced pressure, filtered, and subjected to a steam distillation (an amount of steam: 2%) for 30 min at 180° C. to give a purified oil.

Thus, the crude oil was prepared from the soybean material containing 70% by weight of the germ content, the crude and purified oils from the soybean material containing 40% by weight of the germ content, and the crude and purified oils from the soybean material containing 20% by weight of the germ content. All of these oils are the soybean oil according to the present invention.

Crude oil from the cotyledon part was also prepared in the same way as the above.

Figure 1:
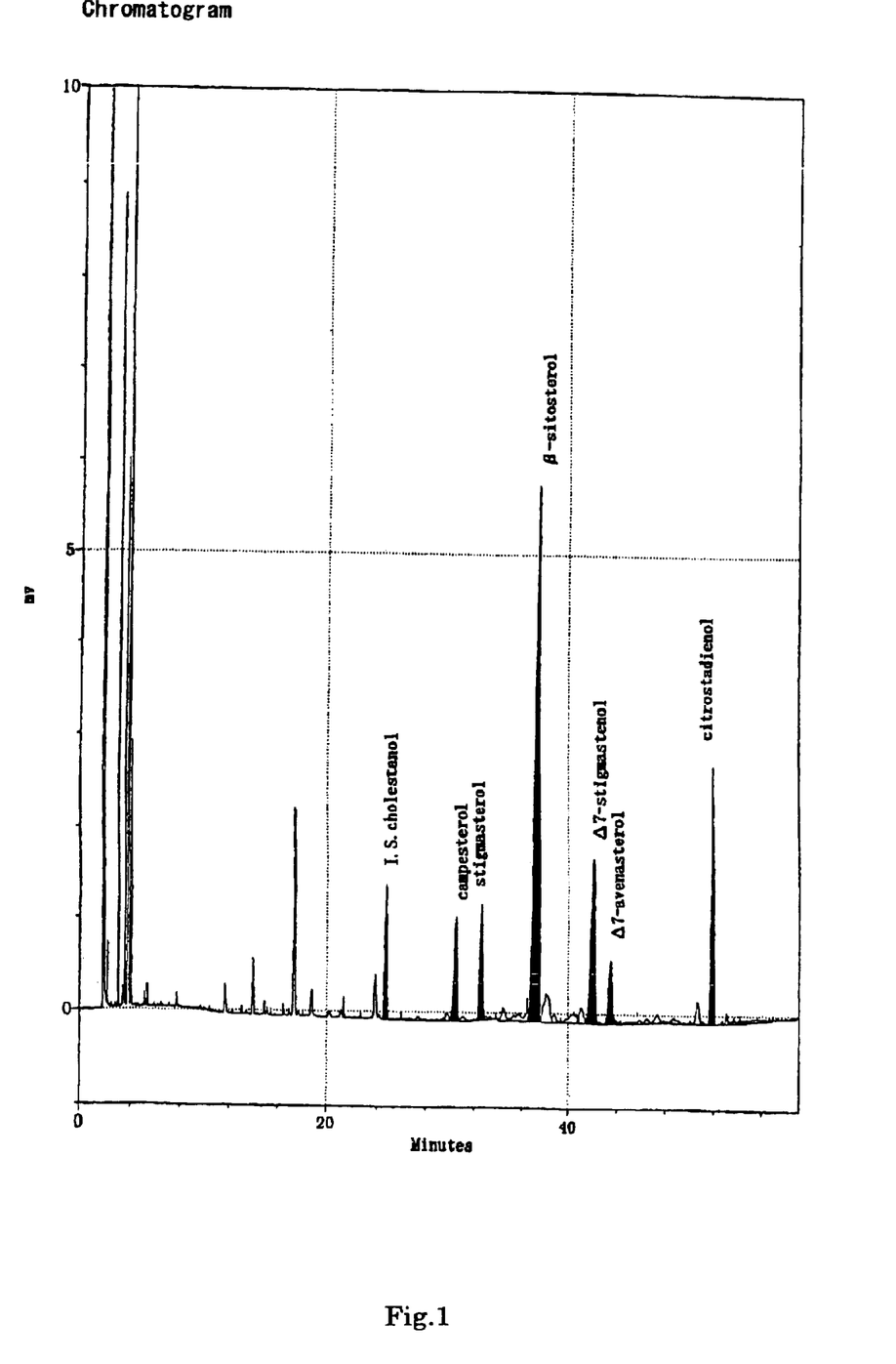
FIG. 1 shows a chart of gas chromatography (GC) of unsaponifiable matters of the soybean oil prepared from thee soybean material containing 40% by weight of the germ content.
Figure 2:
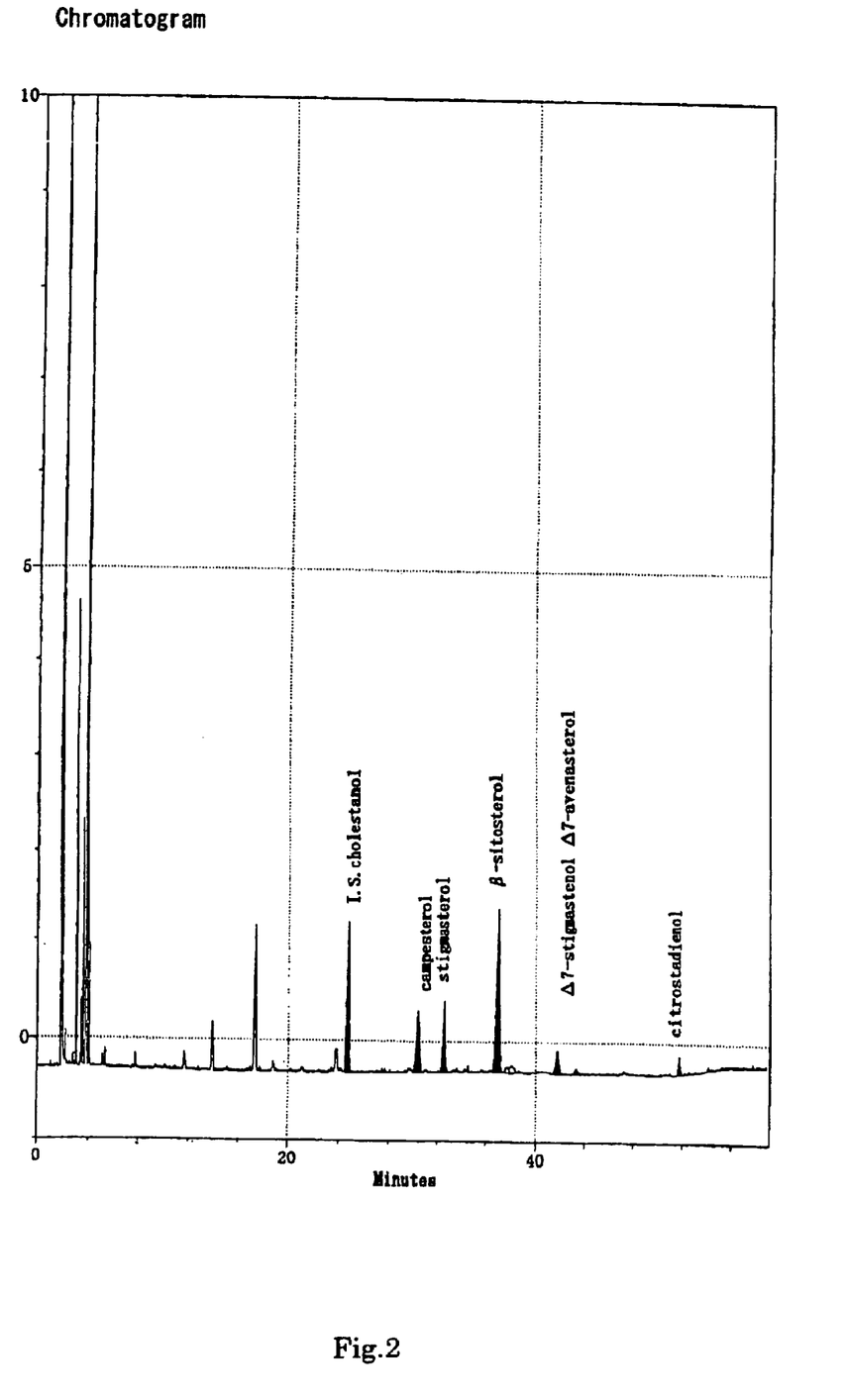
FIG. 2 shows a chart of GC of matters of the usual soybean oil as a comparison.

The contents of sterols, tocopherol and fatty acids of the representative oils are analyzed and summarized in Table 2. FIG. 1 shows a chart of gas chromatography (GC) of unsaponifiable matters of the soybean oil prepared from the soybean material containing 40% by weight of the germ content. FIG. 2 shows a chart of GC of unsaponifiable matters of the usual soybean oil as a comparison. The conditions of GC are shown in below just by way of example.

Detection: FID;

Temperature: Inj. 280° C., Det. 290° C.;

Column 260° C.(50 min)–10° C./min–300° C.(5 min);

Transfer Phase: Helium;

Internal Standard: Cholestanol.

It is demonstrated from FIG. 1 and FIG. 2 that a ratio of peaks appearing later than that of β-Sitosterol, that is, those of Δ7-Stigmastenol, Δ7-Avenasterol, and Citrostadienol, to peaks appearing faster than that of β-Sitosterol, that is, those of Campesterol and Stigmasterol, is relatively higher in FIG. 1 than in FIG. 2.

Thus, the soybean oil according to the present invention is characterized by the following features:

(1) The content of the total sterol is 0.8% by weight or more when the soybean oil is prepared from the soybean material 15% by weight or more of the germ content. Said content is equal to or more than that in usual oils such as soybean oil (0.4% by weight), rapeseed oil (0.8% by weight), corn oil (0.9% by weight), palm oil(0.3% by weight), safflower oil (0.3% by weight);

(2) There are many sterol components whose retention time (r.t.) in GC is later than that of β-Sitosterol, and their contents amount to 20~51% by weight for the total amount of the sterols in the soybean oil;

(3) The ratio (content) of Campesterol in the total sterol is 14% by weight or less, which is lower than those in the soybean oil (20% by weight), rapeseed oil (34% by weight) and corn oil (20% by weight).

TABLE 2

| Materials | Soybean Germ Part (Fraction) | | | | | | Cotyledon Part | Whole Soybeans |
|---|---|---|---|---|---|---|---|---|
| Germ Content (by weight) | 70% | | | 40% | | 20% | | |
| Lot. No. | 1 | 2 | 3 | | | | | |
| Oils | Crude Oil | Crude Oil | Crude Oil | Crude Oil | Purified Oil | Purified Oil | Crude Oil | Soybean Tempura Oil |
| Oil No. | 1 | 2 | 3 | 4 | 5 | 6 | 7 | 8 |
| Total Sterol % | 3.7 (100%) | 3.1 (100%) | 2.9 (100%) | 1.8 (100%) | 1.7 (100%) | 1.0 (100%) | 0.2 | 0.4 |
| β-Sitosterol | 2.0 (54) | 1.6 (55) | 1.5 (51) | 1.0 (56) | 0.9 (53) | 0.5 (53) | 0.1 | 0.2 |
| Stigmasterol | 0.2 (5) | 0.2 (7) | 0.2 (7) | 0.1 (6) | 0.1 (6) | 0.1 (9) | 0.05 | 0.1 |
| Δ7-Stigmastenol | 0.6 (16) | 0.5 (17) | 0.5 (17) | 0.3 (17) | 0.3 (18) | 0.1 (14) | | |
| Campesterol | 0.3 (8) | 0.2 (7) | 0.2 (7) | 0.1 (6) | 0.1 (6) | 0.1 (9) | 0.05 | 0.1 |
| Brasssicasterol | 0.01 (0.3) | 0.01 (0.3) | 0.01 (0.3) | 0.003 (0.2) | 0.003 (0.2) | 0.00 | | |
| Δ7-Avenasterol | 0.3 (8) | 0.2 (7) | 0.2 (7) | 0.1 (6) | 0.1 (6) | 0.05 (5) | 0.0 | 0.0 |
| Citrostadienol | 0.4 (11) | 0.4 (14) | 0.3 (10) | 0.2 (11) | 0.2 (12) | 0.1 (11) | | |
| Cholesterol | 0.01 (0.3) | 0.01 (0.3) | 0.01 (0.3) | 0.003 (0.2) | 0.003 (0.2) | 0.0 | 0.0 | 0.0 |
| Tocopherols mg/Oil 100 g | 230* | 238 | 190 | 143 | 140 | 116 | 76 | 95 |
| Fatty Acid | | | | | | | | |
| 16:0 | 13.0 | 11.9 | 12.3 | 11.5 | 11.9 | 11.2 | 10.9 | 10.4 |
| 18:0 | 3.5 | 3.7 | 3.8 | 4.3 | 4.4 | 4.4 | 4.6 | 4.4 |
| 18:1 | 11.2 | 15.2 | 15.2 | 20.5 | 20.4 | 23.0 | 24.2 | 25.4 |
| 18:2 | 54.8 | 55.6 | 55.5 | 53.5 | 53.6 | 52.7 | 52.1 | 51.5 |
| 18:3 | 17.4 | 13.3 | 12.8 | 9.4 | 9.0 | 7.8 | 6.6 | 6.7 |
| 20:0 | | 0.5 | 0.4 | 0.4 | 0.4 | 0.4 | 0.4 | 0.4 |
| 20:1 | | | 0.0 | 0.4 | 0.4 | 0.4 | 0.2 | 0.3 |

(Animal Test No.1)

By using the oils No.3, 5, 6, 7 and 8 in Table 2 as Test Oils, animal tests were performed to study their serum cholesterol lowering effects according to the following animal test. protocols.

Oil No.8 was used in Tests No.1 and No.2, Oils No.3, 5, 6, and 7 were used in Tests No. 3, 4, 5 and 6, respectively.

No.1 Protocols

Test numbers and their diet compositions are summarized in Table 3.

Male Wistar rats (190~200 g) were housed individually in a cage, for four weeks, freely fed with the diet. Ten rats were used per each of Tests No.1 to No.5, and 6 rats Test No.6

TABLE 3

| Test No. | 1 | 2 | 3 | 4 | 5 | 6 |
|---|---|---|---|---|---|---|
| Addition of Cholesterol | − | + | + | + | + | + |
| Germ Content (%) in the Material | 2 | 2 | 70 | 40 | 20 | 0 |
| Oil Composition of Diet | Soybean Tempura Oil | Soybean Tempura Oil | Crude Oil | Purified Oil | Purified Oil | Cotyledon Oil |
| Oil | 10 g | 10 g | 10 g | 10 g | 10 g | 10 g |
| Sterol Content (g) | (0.04) | (0.04) | (0.27) | (0.14) | (0.09) | (0.02) |
| Cholesterol | — | 0.5 | 0.5 | 0.5 | 0.5 | 0.5 |
| Sodium Cholate | — | 0.25 | 0.25 | 0.25 | 0.25 | 0.25 |
| Casein | 20 | 20 | 20 | 20 | 20 | 20 |
| Sucrose | 60.80 | 60.05 | 60.05 | 60.05 | 60.05 | 60.05 |
| Cellulose | 4 | 4 | 4 | 4 | 4 | 4 |
| Mineral Mix | 4 | 4 | 4 | 4 | 4 | 4 |
| Vitamin Mix | 1 | 1 | 1 | 1 | 1 | 1 |
| Choline Cl | 0.2 | 0.2 | 0.2 | 0.2 | 0.2 | 0.2 |
| (Total) | 100 g | 100 g | 100 g | 100 g | 100 g | 100 g |

Serum Cholesterol Analysis after 2, 3 and 4 Weeks

At the end of the test period, the rats were anesthetized with ethyl ether. Blood was collected from their abdominal aorta and serum was separated from the blood by centrifugation for 15 at 3,000 rpm. The total cholesterol level in the serum was measured by an enzymatic analysis using FUJI DRI-CHEM SLIDE TCHO PII.

(Animal Test Results)

Figure 3:
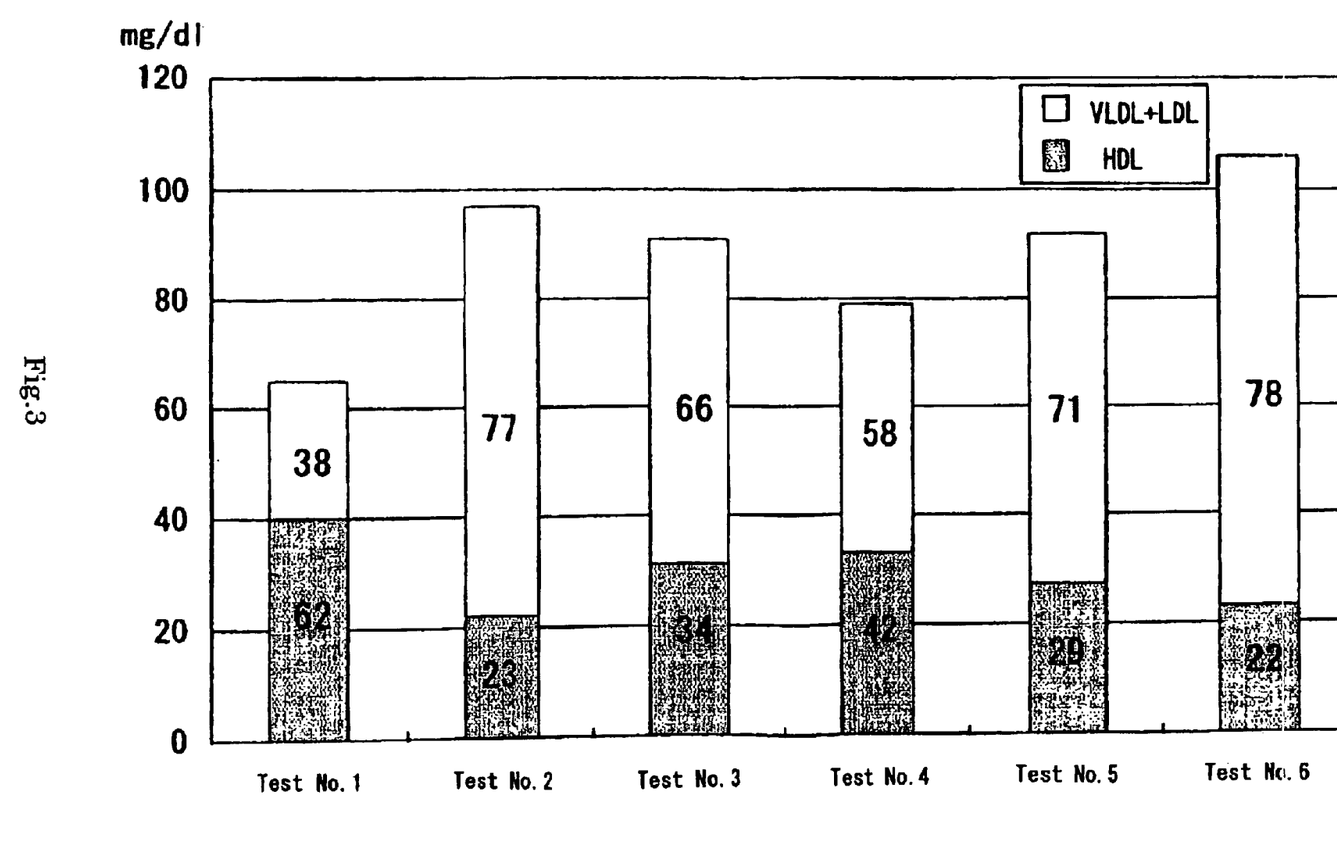
FIG. 3 shows a ratio between the HDL-cholesterol level and the (VDL+LDL)-cholesterol level in serum after 2 week breeding.
Figure 4:
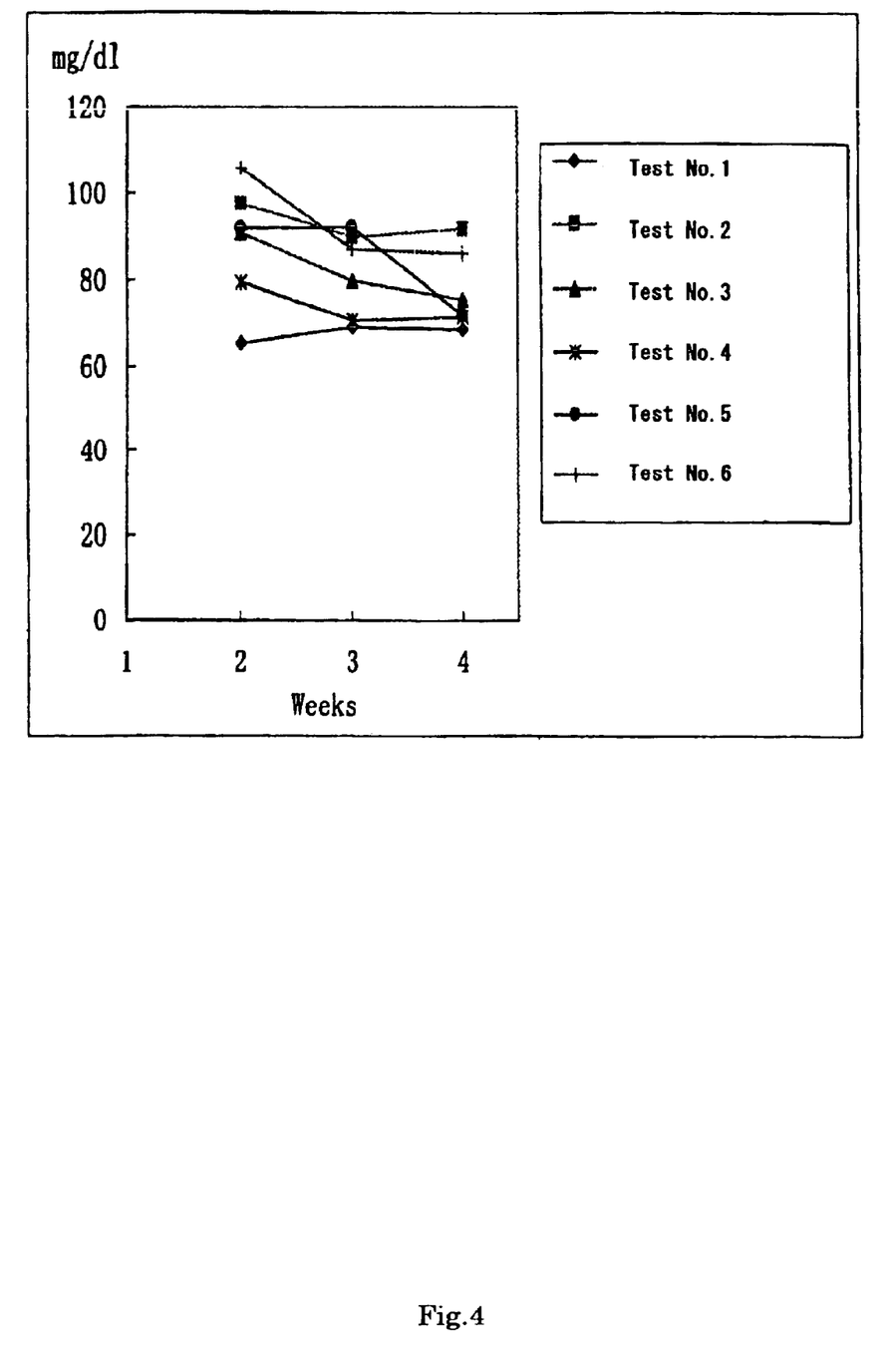
FIG. 4 shows a change of the total cholesterol level in serum in the course of time.
Figure 5:
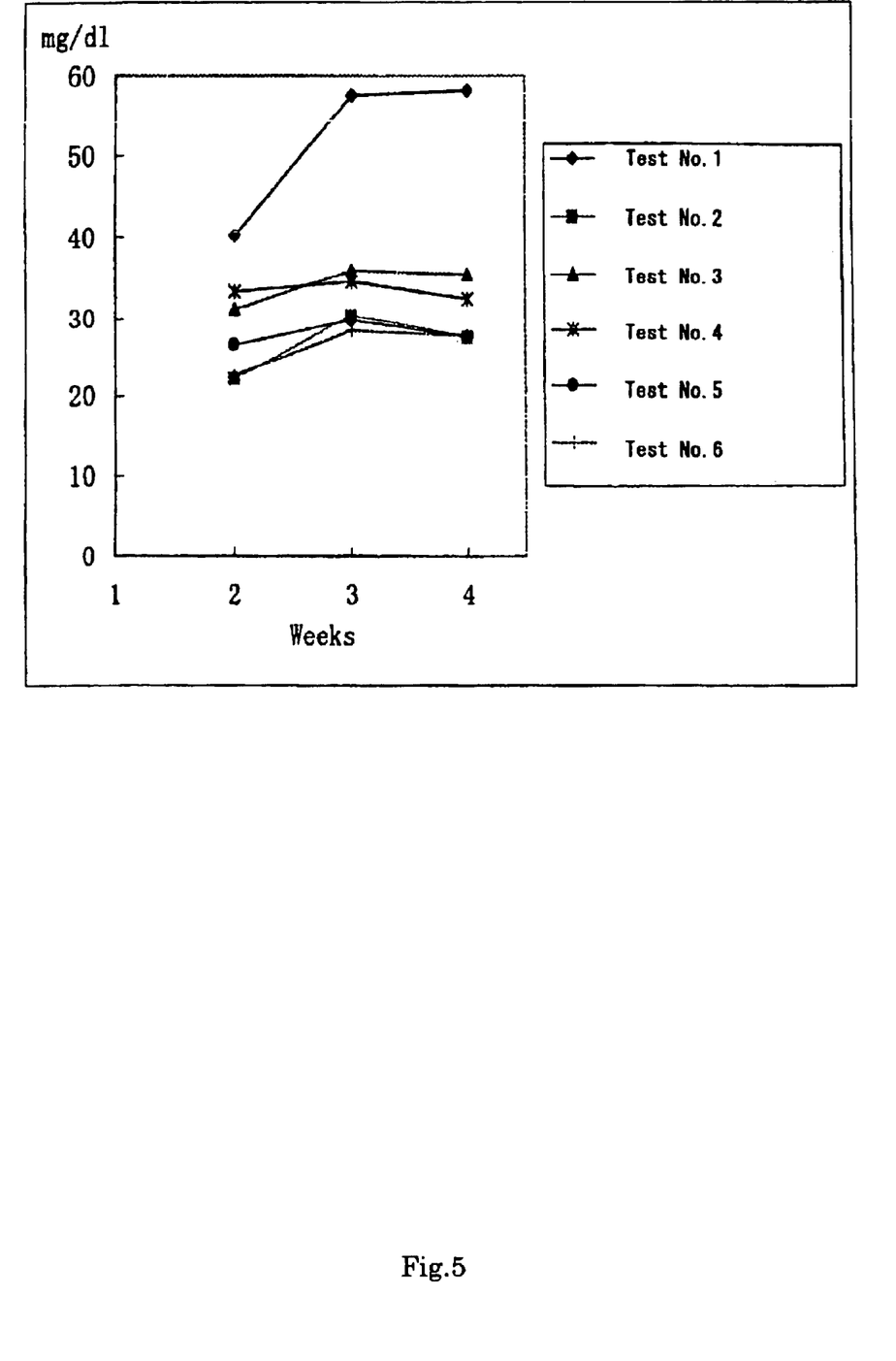
FIG. 5 shows a change of the HDL-cholesterol level in serum in the course of time.

FIG. 3 shows a ratio between a HDL-cholesterol level and (VLDL+LDL)-cholesterol level in the serum after two week housing period. FIG. 4 shows a change of a total cholesterol level in the serum during the course of time. FIG. 5 shows a change of the HDL-cholesterol level in the serum during the course of time.

As seen from FIG. 3, Test No.4 showed the secondarily highest HDL-cholesterol level and the secondarily lowest (VLDL+LDL)-cholesterol level, while Test No.1 (cholesterol was not supplemented) had the highest HDL-cholesterol level and the lowest (VLDL+LDL)-cholesterol level.

As seen from FIG. 4, Test No.4 showed the lowest total cholesterol level in the serum among various kinds of the soybean oil throughout 2, 3, and 4 weeks housing periods, followed by Test No.3, NO.5, No.2 and No.6.

As seen from FIG. 5, Test No.3 and No.4 similarly showed the highest HDL-cholesterol level in the serum, followed by Test No.5, No.2 and No.6.

As seen from Table 3, although the total sterol content contained in Test No.4 is about half that in Test No.3, Test No.4 showed the lowest total cholesterol level in the serum throughout 2, 3, and 4 week housing periods.

The above fact revealed first by the present invention strongly suggests that the cholesterol lowering effects of the soybean oil according to the present invention may be attributed not only to the content of the sterols contained therein.

EXAMPLE 2

Other samples of the soybean oil were prepared according to the present invention. They were used in animal tests for studying the cholesterol lowering effects in which a usual soybean tempura oil supplemented with soybean sterol (containing 60% by weight of β-Sitosterol) was tested as well for comparison.

(Production of Material)

Selected whole soybeans were crudely crushed, and the germ and hull were separated with a large aspirator. The germ part which may contain contaminants such as the hull and cotyledon was then separated from the hull part by means of a large reel. Furthermore, the hull part was removed from the germ part by using a small aspirator. The soybean material thus produced contains about 44.4% by weight, or 48~52% by weight of the germ content (Table 4). Table 4 also shows the content of the cotyledon part.

(Preparation of Oil)

The soybean material produced in the above was flaked by using a flaking roller, extracted with n-hexane by using a small extracting apparatus to give micelle. After removing N-hexane from the micelle in distillation by means of LTV evaporator at 50° C. and 100–150 mmHg, the micelle was concentrated for 6~7 hours and at 60~80° C. by using a capillary evaporator under a reduced pressure with an aspirator, and dried for 3~4 hours at 60~70° C. by using a dryer under a reduced pressure to give the soybean oil (Germ oil) according to the present invention. Similarly, the cotyledon part was treated to give cotyledon oil.

Two lots of the soybean oil (Germ oil) according to the present invention and the cotyledon oil were analyzed and various values obtained in the analysis are summarized in Table 4.

TABLE 4

| | | Experiment I | | Experiment II | |
|---|---|---|---|---|---|
| | | Germ Part | Cotyledon Part | Germ Part | Cotyledon Part |
| Purity in Material | Hull % | 9.0 | 0.4 | Trace | Trace |
| | Cotyledon % | 44.1 | 97.9 | 48~52 | >90 |
| | Germ % | 44.4 | 0.6 | 48~52 | 0.4~0.6 |
| | Others % | 2.5 | 1.1 | | |
| Analysis of Oil | Oil (%) in Material | 12.4 | 21.2 | 12~15 | 20~23 |
| | Total Sterol % | 2.25 | 0.21 | 2.59 | 0.198 |
| | Tocopherol % | 0.223 | 0.144 | 0.214 | 0.142 |
| | Palmitic Acid % | 13.0 | 12.8 | | |
| | Stearic Acid % | 3.5 | 4.6 | | |
| | Oleic Acid % | 18.2 | 22.7 | | |
| | Linoleic Acid % | 54.3 | 49.3 | | |
| | Linolenic Acid % | 11.0 | 10.6 | | |

(Animal Test No.2)

Experiments I and II were carried out by using the various kinds of the oil prepared in the above according to the following protocols to study the cholesterol lowering effects. The diet compositions are summarized in Tables 5 and 6. The cotyledon oil and soybean tempura oil were used as a control, and the cotyledon oil and soybean tempura oil supplemented with β-sterol were used as a positive control as well. All the figures in these Tables mean "% by weight."

TABLE 5

Experiment I Diet composition (%)

| | Test No. | | | |
|---|---|---|---|---|
| | 1 Germ Oil | 2 Cotyledon Oil | 3 Soybean Tempura Oil | 4 (Soybean Tempura Oil + β-Sitosterol) |
| Germ Content (%) in the Material | 44.4 | 0 | 2 | 2 |
| Oil (g) | Germ Oil 9.0 | Cotyledon Oil 9.0 | Soybean Tempura Oil 9.0 | Soybean Tempura Oil 9.0 |
| (Sterol Content) | (0.20) | (0.02) | (0.04) | (0.04) |
| β-Sitosterol | — | — | — | 2.2 |
| Cholesterol | 0.5 | 0.5 | 0.5 | 0.5 |
| Cholic acid | 0.15 | 0.15 | 0.15 | 0.15 |
| Casein | 22.0 | 22.0 | 22.0 | 22.0 |
| Cellulose | 5.0 | 5.0 | 5.0 | 5.0 |
| Salts | 5.0 | 5.0 | 5.0 | 5.0 |
| Vitamin mix | 0.5 | 0.5 | 0.5 | 0.5 |
| Choline Cl | 0.3 | 0.3 | 0.3 | 0.3 |
| Sucrose | 57.55 | 57.55 | 57.55 | 55.35 |

TABLE 6

Experiment II Diet composition (%)

| | Test No. | | | | |
|---|---|---|---|---|---|
| | 1 Germ Oil | 2 Cotyledon Oil | 3 Soybean Tempura Oil | 4 (Cotyledon + β-Sitosterol) | 5 Beef Tallow |
| Germ Content (%) in the Material | 48~52 | 0 | 2 | 0 | — |
| Oil (g) | Germ Oil 9.0 | Cotyledon Oil 9.0 | Soybean Tempura Oil 9.0 | Cotyledon Oil 9.0 | Beef Tallow 9.0 |
| Sterol Content | (0.23) | (0.02) | (0.04) | (0.02) | — |
| β-Sitosterol | — | — | — | 2.2 | — |
| Cholesterol | 0.5 | 0.5 | 0.5 | 0.5 | 0.5 |
| Cholic acid | 0.15 | 0.15 | 0.15 | 0.15 | 0.15 |
| Casein | 22.0 | 22.0 | 22.0 | 22.0 | 22.0 |
| Cellulose | 5.0 | 5.0 | 5.0 | 5.0 | 5.0 |
| Salts | 5.0 | 5.0 | 5.0 | 5.0 | 5.0 |
| Vitamin mix | 0.5 | 0.5 | 0.5 | 0.5 | 0.5 |
| Choline Cl | 0.3 | 0.3 | 0.3 | 0.3 | 0.3 |
| Sucrose | 57.55 | 57.55 | 57.55 | 55.35 | 57.55 |

The purity of β-sterol (manufactured by Tokyo Kasei Co.) used in the above Tables is about 60% and the rest consists of Campesterol.

No.2 Protocols

Three Male Wistar rats (Experiment I: ca.190 g, Experiment II: 190~200 g) were housed in a cage for four weeks, freely fed with the diet. Nine rats per each of Tests. The results are shown in Table 7.

β-Sitosterol (Tokyo Kasei Co.) has a purity of about 60%, and the rest being Campesterol. The cholesterol level in the serum was determined in the same way as in Example 1, and the cholesterol level in the liver was determined according to a method of Rudel et al., (Rudel, L. L., et al., J. Lipid Res., 14, 364 (1973)).

TABLE 7

Experiment I Results

| Test No. | Sterol (%/diet) | Serum Cholesterol (mg/dl) | Hepatic Cholesterol (mg/g wt) |
|---|---|---|---|
| No. 1 Germ Oil | 0.20 | 110.6 ± 8.8 | 14.03 ± 2.11 |
| No. 2 Cotyledon Oil | 0.02 | 151.1 ± 19.3 | 18.56 ± 3.61 |
| No. 3 Soybean Tempura Oil | 0.04 | 121.1 ± 10.0 | 15.60 ± 1.43 |
| No. 4 Soybean Tempura Oil + β-Sitosterol | 0.04 + 2.2 = 2.24 | 118.8 ± 7.6 | 5.71 ± 0.81 |
| No. 5 (Reference) Clea diet | | 83.8 ± 6.0 | 2.59 ± 0.11 |

Experiments II Results

| Test No. | Sterol (%/diet) | Serum Sterol (mg/dl) | Hepatic Sterol (mg/g wt) |
|---|---|---|---|
| No. 1 Germ Oil | 0.23 | 102.2 ± 11.3 | 14.29 ± 3.81 |
| No. 2 Cotyledon Oil | 0.02 | 116.0 ± 12.5 | 22.13 ± 7.37 |
| No. 3 Soybean Tempura Oil | 0.04 | 109.9 ± 6.2 | 21.44 ± 7.50 |
| No. 4 Cotyledon Oil + β-Sitosterol | 0.02 + 2.2 = 2.22 | 124.2 ± 9.4 | 5.71 ± 1.75 |
| No. 5 Beef Tallow | | 181.7 ± 20.1 | 17.11 ± 1.43 |
| No. 6 (Reference) Clea diet | | 77.3 ± 10.6 | 1.88 ± 0.53 |

("Clea diet" in the above Tables is a commercially available diet for animals, which does not contain cholesterol)

As seen from Table 7, the cholesterol levels in the serum and liver in the case of Germ oil (Test No.1) were significantly lower than those in the case of Cotyledon oil (Test No.2) or the soybean tempura oil in both Experiments I and II.

The soybean tempura oil (Experiment I, No.4) supplemented with β-Sitosterol in an amount of 4 times as much as the sterol content of the germ oil (Test NO.1) and the cotyledon oil (Experiment II, No.4) supplemented with β-Sitosterol in an amount of 4 times as much as the sterol content of the germ oil (Test NO.1) showed a significantly lower cholesterol level than the Germ oil in the liver, but in the serum.

These results may demonstrate that the serum cholesterol lowering effects of the soybean oil according to the present invention can not be attributed solely to β-Sitosterol contained therein, strongly suggesting that there may be other serum chlolesterol-lowering components in the soybean oil according to the present invention.

EXAMPLE 3

The soybean oil prepared in Example 1 (the crude oil prepared from the soybean material containing 40% by weight of the germ content and the purified oil obtained therefrom), soybean tempura oil, rice bran oil and corn oil were tested with respect to their serum cholesterol lowering effects according to the following animal test protocols. The figures of the components in Table 8 mean "% by weight."

TABLE 8

Diet composition (%)

| | Test No. | | | | |
|---|---|---|---|---|---|
| | 1 Soybean Tempura Oil | 2 Rice Bran Oil | 3 Corn Oil | 4 Soybean Germ Part (Crude Oil) | 5 Soybean Germ Part (Purified Oil) |
| Oil (g) | 10.0 | 10.0 | 10.0 | 10.0 | 10.0 |
| Sterol Content | (0.04) | (0.11) | (0.09) | (0.15) | (0.14) |
| Cholesterol | — | 0.5 | 0.5 | 0.5 | 0.5 |
| Sodium Cholate | — | 0.25 | 0.25 | 0.25 | 0.25 |
| Casein | 20 | 20 | 20 | 20 | 20 |
| Sucrose | 60.80 | 60.05 | 60.05 | 60.05 | 60.05 |
| Cellulose | 4 | 4 | 4 | 4 | 4 |
| Mineral Mix | 4 | 4 | 4 | 4 | 4 |
| Vitamin mix | 1 | 1 | 1 | 1 | 1 |
| Choline Cl | 0.2 | 0.2 | 0.2 | 0.2 | 0.2 |
| Total | 100 | 100 | 100 | 100 | 100 |

No.3 Protocols

Male Sprague Dawley (SD) rats (135 g) were individually housed in a cage for four weeks, freely fed with the diet. Ten rats per each of Tests. The results are shown in Table 9.

TABLE 9

| Test No. | Cholesterol | Serum Total Sterol after 4 weeks (mg/dl) | Serum LDL Sterol After 4 weeks (mg/dl) |
|---|---|---|---|
| No. 1 Soybean Tempura Oil | − | 68 ± 10 | 4 ± 1 |
| No. 2 Rice Bran Oil | + | 146 ± 29 | 34 ± 8 |
| No. 3 Corn Oil | + | 129 ± 47 | 29 ± 12 |
| No. 4 Soybean Germ Part (Crude Oil) | + | 100 ± 34 | 21 ± 10 |
| No. 5 Soybean Germ Part (Purified Oil) | + | 98 ± 16 | 22 ± 6 |

As seen from Table 9, both the total cholesterol and LDL-cholesterol levels in the serum in the case of the soybean oil (Germ oil) were significantly lower than those in the case of the rice bran oil and corn oil that are known to have the cholesterol lowering effects, demonstrating that the serum cholesterol lowering effect of the soybean oil according to the present invention are significantly superior to those of the rice bran oil and corn oil.

The serum cholesterol was determined in the same way as in Example 1.

Industrial Applicability

The cholesterol lowering effects of soybean sterol are obtained by administrating it at an amount of three times as much as the cholesterol content in the diet (Yasui, A., Kaneda, T., J. Jap. Soc. Food and Nutr., Vol.25, No.1 27–32 (1973)).

On the other hand, the sterol contained in the soybean oil according to the present invention does show the cholesterol lowering effects, event though its content is much lower than, i.e., less than half the cholesterol content in the diet, as seen from FIGS. 3–5, and Table 7.

The cholesterol lowering effects of the present soybean oil are very remarkable, and never expected from the prior observations.

Furthermore, the above results suggest that there may be other cholesterol-lowering components than the soybean sterol (β-Sitosterol) in the soybean oil according to the present invention.

What is claimed is:

1. An oil prepared from a soybean material wherein said soybean material has a germ content of 15 to 80% by weight, and wherein said oil comprises a total content of Δ7-Stigmastenol, Δ7-Avenasterol, and Citrostadienol of 20–51% by weight, based on the total weight of sterol.

2. The oil of claim 1, wherein said soybean material has a germ content of 30 to 80% by weight.

3. The oil according to claim 2, which comprises Campesterol in an amount of 7.0–14% by weight or less, based on the total weight of sterol.

4. The oil according to claim 3 which comprises tocopherol in an amount of 100 mg or more per 100 g of said oil.

5. The oil according to claim 2 which comprises tocopherol in an amount of 100 mg or more per 100 g of said oil.

6. The oil according to claim 1, which comprises Campesterol in an amount of 7.0–14% by weight or less, based on the total weight of sterol.

7. The oil according to claim 6 which comprises tocopherol in an amount of 100 mg or more per 100 g of said oil.

8. The oil according to claim 1 which comprises tocopherol in an amount of 100 mg or more per 100 g of said oil.

9. An oil prepared from a soybean material wherein said soybean material has a germ content of 15 to 80% by weight and wherein said soybean material is produced by crudely crushing a starting soybean material or its selected seeds from which foreign substances have been removed, into a size of less than ½, and separating and concentrating a soybean germ fraction, and wherein said oil comprises a total content of Δ7-Stigmastenol, Δ7-Avenasterol, and Citrostadienol of 20–51% by weight, based on the total weight of sterol.

10. The oil according to claim 9, which comprises Campesterol in an amount of 7.0–14% by weight or less, based on the total weight of sterol.

11. The oil according to claim 10 which comprises tocopherol in an amount of 100 mg or more per 100 g of said oil.

12. The oil according to claim 9 which comprises tocopherol in an amount of 100 mg or more per 100 g of said oil.

13. An oil prepared from a soybean material without any addition of sterol, which contains 0.8% by weight or more of a total sterol content, and wherein said oil comprises a total content of Δ7-Stigmastenol, Δ7-Avenasterol, and Citrostadienol of 20–51% by weight, based on the total weight of sterol.

14. The oil according to claim 13, which comprises Campesterol in an amount of 7.0–14% by weight or less, based on the total weight of sterol.

15. The oil according to claim 14 which comprises tocopherol in an amount of 100 mg or more per 100 g of said oil.

16. The oil according to claim 13 which comprises tocopherol in an amount of 100 mg or more per 100 g of said oil.

17. A food comprising an oil prepared from a soybean material, wherein said soybean material has a germ content of 15% by weight or more, and wherein said oil comprises a total content of Δ7-Stigmastenol, Δ7-Avenasterol, and Citrostadienol of 20–51% by weight, based on the total weight of sterol.

18. An oil prepared from a soybean material wherein said soybean material has a germ content of 15 to 80% by weight and wherein said soybean material is produced by crudely crushing a starting soybean material or its selected seeds from which foreign substances have been removed, into a size of less than ½, flaking them, and separating and concentrating a soybean germ fraction, and wherein said oil comprises a total content of Δ7-Stigmastenol, Δ7-Avenasterol, and Citrostadienol of 20–51% by weight, based on the total weight of sterol.

19. The oil according to claim 18, which comprises Campesterol in an amount of 7.0–14% by weight or less, based on the total weight of sterol.

20. The oil according to claim 19 which comprises tocopherol in an amount of 100 mg or more per 100 g of said oil.

21. The oil according to claim 18 which comprises tocopherol in an amount of 100 mg or more per 100 g of said oil.

* * * * *